United States Patent [19]
Pommer et al.

[11] 3,992,548
[45] Nov. 16, 1976

[54] FUNGICIDAL COMPOSITION

[75] Inventors: Ernst Heinrich Pommer; Juergen Kradel, both of Limburgerhof; Rudolf Polster, Frankenthal, all of Germany

[73] Assignee: BASF Aktiengesellschaft, Ludwigshafen (Rhine), Germany

[22] Filed: May 31, 1974

[21] Appl. No.: 474,899

[30] Foreign Application Priority Data
June 7, 1973 Germany............................ 2329034

[52] U.S. Cl.................................. 424/274; 424/16; 424/23; 424/168; 424/286; 424/309; 424/357
[51] Int. Cl.²...................... A01N 9/22; A61K 31/40
[58] Field of Search..................... 424/286, 274, 309

[56] References Cited
UNITED STATES PATENTS

| | | | |
|---|---|---|---|
| 2,504,404 | 4/1950 | Flenner............................. | 424/286 |
| 3,436,456 | 1/1969 | Louis et al......................... | 424/286 |
| 3,441,581 | 4/1969 | Windel et al....................... | 424/286 |
| 3,461,209 | 8/1969 | Frensch et al.................... | 424/286 X |
| 3,472,936 | 10/1969 | Goeldner et al................. | 424/286 X |

FOREIGN PATENTS OR APPLICATIONS 1,218,792    6/1966    Germany............................ 424/309

OTHER PUBLICATIONS

The Merck Index, 1968, 8th Edition, pp. 203 & 468.
Pesticide Index 1964, 4th Edition, pp. 88 & 233.

*Primary Examiner*—Dale R. Ore
*Attorney, Agent, or Firm*—Johnston, Keil, Thompson & Shurtleff

[57] ABSTRACT

A valuable fungicidal composition consisting essentially of (a) diisopropyl 3-nitroisophthalate, (b) a dithiocarbamate and/or (c) a compound selected from the group consisting of N-thiotrichloromethylphthalamide and N-thiotrichlormethyl-tetrahydrophthalimide.

5 Claims, No Drawings

FUNGICIDAL COMPOSITION

The present invention relates to a fungicide containing a composition of different active ingredients.

It is known to use diisopropyl 3-nitroisophthalate (German Pat. No. 1,218,792) and dithiocarbamates (U.S. Pat. No. 2,504,404) as fungicides.

We have now found that a fungicide containing a composition of a. diisopropyl 3-nitroisophthalate and
b. a dithiocarbamate selected from the group consisting of manganese ethylenebisdithiocarbamate (maneb); manganese zinc ethylenebisdithiocarbamate (mancozeb);

zinc ethylenebisdithiocarbamate (zineb);
zinc-(N,N'-propylenebisdithiocarbamate) (propineb);
ammonia complex of zinc-(N,N'-ethylenebisdithiocarbamate) and N,N'-polyethylenebis-(thiocarbamoyl)-disulfide (metiram);
ammonia complex of zinc-(N,N'-propylenebisdithiocarbamate) and N,N'-polypropylenebis-(thiocarbamoyl)-disulfide (methyl metiram); and
tetramethylthiuram disulfide (TMTD), and/or
c. a substituted phthalimide selected from the group consisting of N-thiotrichloromethyl tetrahydrophthalimide (captan) and N-thiotrichloromethyl phthalimide (folpet), has a much better fungicidal action than its individual components.

The fungicides according to the invention are particularly suitable for controlling and especially for curing plant diseases caused by powdery mildews such as *Erysiphe cichoriacearum* in cucurbitaceae, *Uncinula necator* in vines, and *Podosphaera leucotricha* in apples.

The ratio of the active ingredients to each other may vary within wide limits; it is, however, preferred to use a ratio by weight of a:b or c of from 2:1 to 1:4, especially 1:1 and 1:2.

When the compositions according to the invention are used for treating plants, application rates are from 0.5 to 6 kg per hectare. Application may be effected for instance in the form of directly sprayable solutions, powders, suspensions, dispersions, emulsions, oil dispersions, pastes or dusts. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coaltar oils and oils of vegetable or mineral origin, aliphatic, cyclic and aromatic hydrocarbons such as benzene, toluene, xylene, paraffin, tetrahydronaphthalene, alkylated naphthalenes, methanol, ethanol, propanol, butanol, chloroform, carbon tetrachloride, cyclohexanol, cyclohexanone, chlorobenzene, isophorone, etc., and strongly polar solvents such as dimethylformamide and dimethyl sulfoxide are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples or surfactants are: alkali metal, alkaline earth metal and ammonium salts of ligningsulfonic acid, naphthalenesulfonic acids, phenolsulfonic acids, alkylaryl sulfonates, alkyl sulfates, and alkyl sulfonates, alkali metal and alkaline earth metal salts or dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders and dusts may be prepared by mixing or grinding the active ingredients with a solid carrier.

Broadcasting agents may be prepared by mixing the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, preferably from 0.5 to 90% by weight of a composition of the invention.

There may be added to the compositions oils of various types, fungicides, nematocides, insecticides, bactericides, trace elements, fertilizers, antifoams (e.g., silicones), growth regulators and other compounds.

These agents (either one or several from the same or different groups of substances) may be added to the fungicides according to the invention in a ratio by weight of from 1:10 to 10:1. The same applies to oils, fungicides, nematocides, insecticides, bactericides, trace elements, fertilizers, antifoams and growth regulators.

EXAMPLE 1

Fully developed leaves of cucumber plants kept in a greenhouse at a temperature of from 22° to 25° C and a relative humidity of from 60° to 70° C are artificially infected by dusting them with conidia of the fungus *Erysiphe cichoriacearum* (cucumber powdery mildew). After an incubation period of 8 to 10 days small almost circular fungus mycelium colonies having a diameter of 3 to 8 and more millimeters become plainly visible on the upper surfaces of the leaves. At this point the leaves are treated by spraying them with aqueous suspensions of compositions of the active ingredients in the mixture and weight ratios given in the table; the individual components are used as comparative agents. Six days after spraying the action of the agents is assessed in accordance with the following scale:
0 = no action (control)
1 = fungus growth checked
2 = at least 50% of fungus destroyed
3 = fungus completely destroyed

| Active ingredient | Ratio | Amount of active ingredient | Action |
|---|---|---|---|
| diisopropyl 3-nitroisophthalate | — | 0.05 | 0 |
|  | — | 0.1 | 1 |
|  | — | 0.2 | 1 |
| maneb | — | 0.05 | 0 |
|  | — | 0.1 | 0 |
|  | — | 0.2 | 0 |
| mancozeb | — | 0.05 | 0 |
|  | — | 0.1 | 0 |
|  | — | 0.2 | 0 |
| zineb | — | 0.05 | 0 |
|  | — | 0.1 | 0 |
|  | — | 0.2 | 0 |
| propineb | — | 0.05 | 0 |
|  | — | 0.1 | 0 |
|  | — | 0.2 | 1 |
| metiram | — | 0.05 | 0 |
|  | — | 0.1 | 0 |
|  | — | 0.2 | 1 |
| methyl metiram | — | 0.05 | 0 |
|  | — | 0.1 | 0 |
|  | — | 0.2 | 0 |
| TMTD | — | 0.05 | 0 |
|  | — | 0.1 | 0 |
|  | — | 0.2 | 1 |
| captan | — | 0.05 | 0 |
|  | — | 0.1 | 0 |
|  | — | 0.2 | 0 |
| folpet | — | 0.05 | 0 |
|  | — | 0.1 | 0 |
|  | — | 0.2 | 0 |

| diisopropyl 3-nitroisophthalate | Ratio | Amount of active ingredient in spray liquor in % | Action |
|---|---|---|---|
| + maneb | 1 : 2 | 0.05 + 0.1 | 2 |
|  | 1 : 4 | 0.05 + 0.2 | 3 |
|  | 1 : 1 | 0.1 + 0.1 | 2 |
|  | 1 : 2 | 0.1 + 0.2 | 3 |
| + mancozeb | 1 : 1 | 0.1 + 0.1 | 2 |
|  | 1 : 2 | 0.1 + 0.2 | 3 |
| + zineb | 1 : 4 | 0.05 + 0.2 | 2 |
|  | 1 : 1 | 0.1 + 0.1 | 2 |
|  | 1 : 1 | 0.1 + 0.1 | 2 |
| + propineb | 1 : 2 | 0.1 + 0.2 | 3 |
|  | 1 : 4 | 0.05 + 0.2 | 2 |
| + metiram | 1 : 1 | 0.1 + 0.1 | 3 |
|  | 1 : 2 | 0.1 + 0.2 | 3 |
| + methyl metiram | 1 : 1 | 0.1 + 0.1 | 2 |
|  | 1 : 2 | 0.1 + 0.2 | 2 |
|  | 2 : 1 | 0.1 + 0.05 | 2 |
| + TMTD | 1 : 1 | 0.1 + 0.1 | 3 |
|  | 1 : 2 | 0.1 + 0.2 | 3 |
|  | 1 : 4 | 0.05 + 0.2 | 2 |
| + captan | 1 : 1 | 0.1 + 0.1 | 3 |
|  | 1 : 2 | 0.1 + 0.2 | 3 |
|  | 1 : 2 | 0.05 + 0.1 | 3 |
| + folpet | 1 : 4 | 0.05 + 0.2 | 3 |
|  | 1 : 1 | 0.1 + 0.1 | 3 |
|  | 1 : 1 | 0.2 + 0.2 | 3 |
| control (untreated) | — | — | — |

EXAMPLE 2

Fully developed leaves of potted vines of the "Muller-Thurgau" variety are, as described in Example 1, artificially infected with conidia of the fungus Uncinula necator (grape powdery mildew). After an incubation period of 12 to 14 days small almost circular fungus mycelium colonies having a diameter of several millimeters become clearly visible on the upper surfaces of the leaves. At this point the leaves are treated, and the results assessed, in the same manner as described in Example 1.

| Active ingredient | Ratio | Amount of active ingredient in spray liquor in % | Action |
|---|---|---|---|
| diisopropyl 3-nitroisophthalate | — | 0.05 | 0 |
|  | — | 0.1 | 1 |
|  | — | 0.2 | 1 |
| methyl metiram | — | 0.05 | 0 |
|  | — | 0.1 | 0 |
|  | — | 0.2 | 1 |
| folpet | — | 0.05 | 0 |
|  | — | 0.1 | 0 |
|  | — | 0.2 | 0 |
| diisopropyl 3-nitroisophthalate |  |  |  |
| + methyl metiram | 1 : 2 | 0.05 + 0.1 | 2 |
|  | 1 : 1 | 0.1 + 0.1 | 2 |
|  | 1 : 2 | 0.1 + 0.2 | 3 |
| + folpet | 1 : 2 | 0.05 + 0.1 | 2 |
|  | 1 : 1 | 0.1 + 0.1 | 2 |
|  | 1 : 2 | 0.1 + 0.2 | 3 |
| control (untreated) | — | — | 0 |

EXAMPLE 3

Fully developed leaves of apple seedlings are, as described in Example 1, artificially infected with conidia of the fungus Podosphaera leucotricha (apple powdery mildew). After an incubation period of 8 to 10 days small almost circular fungus mycelium colonies having a diameter of 3 to 6 millimeters become clearly visible on the upper surfaces of the leaves. At this point the leaves are treated, and the results assessed, in the same manner as described in Example 1.

| Active ingredient | Ratio | Amount of active ingredient in spray liquor in % | Action |
|---|---|---|---|
| diisopropyl 3-nitroisophthalate | — | 0.05 | 0 |
|  | — | 0.1 | 0 |
|  | — | 0.2 | 1 |
| metiram | — | 0.05 | 0 |
|  | — | 0.1 | 0 |
|  | — | 0.2 | 0 |
| captan | — | 0.05 | 0 |
|  | — | 0.1 | 0 |
|  | — | 0.2 | 0 |
| diisopropyl 3-nitroisophthalate |  |  |  |
| + metiram | 1 : 2 | 0.05 + 0.1 | 2 |
|  | 1 : 1 | 0.1 + 0.1 | 2 |
|  | 1 : 2 | 0.1 + 0.2 | 3 |
| + captan | 1 : 2 | 0.05 + 0.1 | 2 |
|  | 1 : 1 | 0.1 + 0.1 | 3 |
|  | 1 : 2 | 0.1 + 0.2 | 3 |
| + metiram + captan | 1 : 1 | 0.1 + 0.05 + 0.05 | 3 |
| control (untreated) | — | — | 0 |

We claim:
1. A fungicidal composition comprising
   a. diisopropyl 3-nitroisophthalate and
   b. a dithiocarbamate selected from the group consisting of
      manganese ethylenebisdithiocarbamate;
      manganese zinc ethylenebisdithiocarbamate;
      zinc ethylenebisdithiocarbamate;
      zinc-(N,N'-propylenebisdithiocarbamate);
      ammonia complex of zinc-(N,N'-ethylenebisdithiocarbamate) and N,N'-polyethylenebis-(thiocarbamoyl)-disulfide;

ammonia complex of zinc-(N,N'-propylenebisdithiocarbamate) and N,N'-polypropylenebis-(thiocarbamoyl)-disulfide; and tetramethylthiuram disulfide, and/or c. a compound selected from the group consisting of N-thiotrichloromethyl tetrahydrophthalimide and N-thiotrichloromethyl phthalimide, the weight ratio of a to b and/or c being from about 1:1 to 1:4.

2. A composition as claimed in claim 1 wherein said weight ratio is about 1:1 to 1:2.

3. A composition as claimed in claim 1 consisting essentially of
   a. diisopropyl 3-nitroisophthalate and
   b. ammonia complex of zinc-(N,N'-ethylenebisdithiocarbamate) and N,N'-polyethylenebis-(thiocarbamoyl)-disulfide and/or
   c. N-thiotrichloromethyl tetrahydrophthalimide.

4. A composition as claimed in claim 1 consisting essentially of
   a. diisopropyl 3-nitroisophthalate and
   b. ammonia complex of zinc-(N,N'-ethylenebisdithiocarbamate) and N,N'-polyethylenebis-(thiocarbamoyl)-disulfide.

5. A composition as claimed in claim 1 consisting essentially of
   a. diisopropyl 3-nitroisophthalate and
   b. N-thiotrichloromethyl tetrahydrophthalimide.

* * * * *